(12) United States Patent
Miller et al.

(10) Patent No.: US 6,416,484 B1
(45) Date of Patent: Jul. 9, 2002

(54) BIOPSY EXTRACTOR

(75) Inventors: Michael E. Miller, Trafalgar; Dan Ireland, Martinsville, both of IN (US)

(73) Assignee: Promex, Inc., Franklin, IN (US)

( * ) Notice: Subject to any disclaimer, the term of this patent is extended or adjusted under 35 U.S.C. 154(b) by 0 days.

(21) Appl. No.: 09/535,343

(22) Filed: Mar. 24, 2000

(51) Int. Cl.⁷ .............................................. A61B 10/00
(52) U.S. Cl. ...................................... 600/564; 606/167
(58) Field of Search ............................... 600/562, 564, 600/566, 567; 606/167, 170

(56) References Cited

U.S. PATENT DOCUMENTS

| | | | | |
|---|---|---|---|---|
| 1,867,624 A | * | 7/1932 | Hoffman | 600/567 |
| 3,007,471 A | * | 11/1961 | McClure, Jr. | 600/567 |
| 3,175,554 A | * | 3/1965 | Stewart | 600/567 |
| 3,929,123 A | * | 12/1975 | Jamshidi | 600/567 |
| 4,785,826 A | | 11/1988 | Ward | 600/567 |
| 4,926,877 A | * | 5/1990 | Bookwalter | 600/567 |
| 5,333,619 A | | 8/1994 | Burgio | 600/567 |
| 5,357,974 A | * | 10/1994 | Baldridge | 600/567 |
| 5,462,062 A | | 10/1995 | Rubinstein et al. | 600/564 |
| 5,522,398 A | | 6/1996 | Goldenberg et al. | 600/567 |
| 5,595,186 A | | 1/1997 | Rubinstein et al. | 600/564 |
| 5,634,473 A | | 6/1997 | Goldenberg et al. | 600/567 |
| 5,807,277 A | | 9/1998 | Swaim | 600/567 |
| 5,885,226 A | | 3/1999 | Rubinstein et al. | 600/567 |
| 5,910,121 A | * | 6/1999 | Paolo et al. | 600/562 |
| 6,015,391 A | | 1/2000 | Rishton et al. | 600/567 |
| 6,063,037 A | * | 5/2000 | Mittermeier et al. | 600/567 |
| 6,080,115 A | | 6/2000 | Rubinstein | 600/567 |
| 6,110,128 A | * | 8/2000 | Andelin et al. | 600/566 |

* cited by examiner

*Primary Examiner*—Kevin Shaver
*Assistant Examiner*—Charles Marmor, II
(74) *Attorney, Agent, or Firm*—Leagre Chandler & Millard LLP

(57) ABSTRACT

Bone marrow biopsy devices, assemblies and methods are provided for extracting bone marrow tissue samples. The assemblies include an outer cannula or biopsy needle and a biopsy extractor sized for insertion into the proximal end of the outer cannula. The biopsy needle includes a tapered portion at the distal end. The extractor includes a cannula and a distal working end. The distal working end has a diameter larger than the diameter of the tapered portion of the biopsy needle lumen. The working end includes a body portion adjacent the cannula and a cutting head having a cutting tip. A hinge is engaged between the body portion and the cutting tip. The hinge allows the cutting head to bend when pushed into the tapered distal end of the outer cannula allowing the cutting tip to sever the tissue sample.

27 Claims, 10 Drawing Sheets

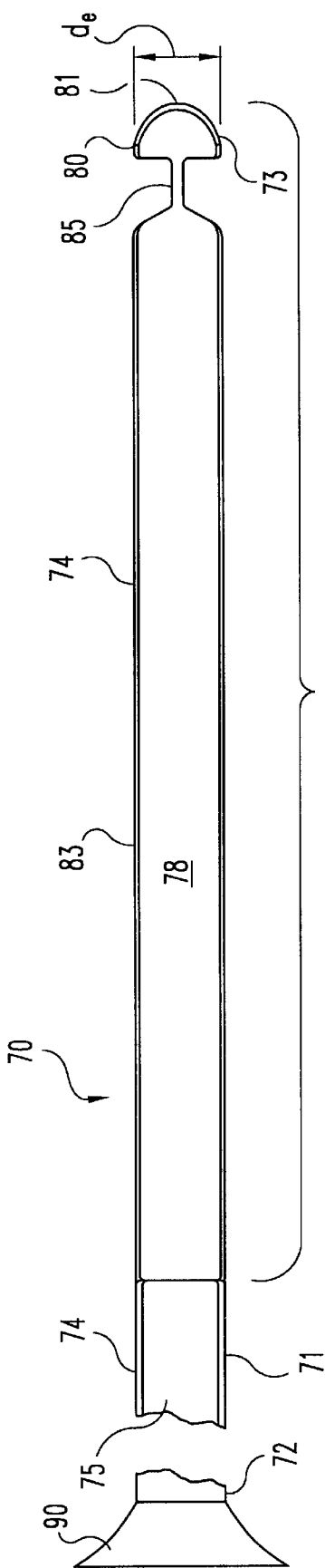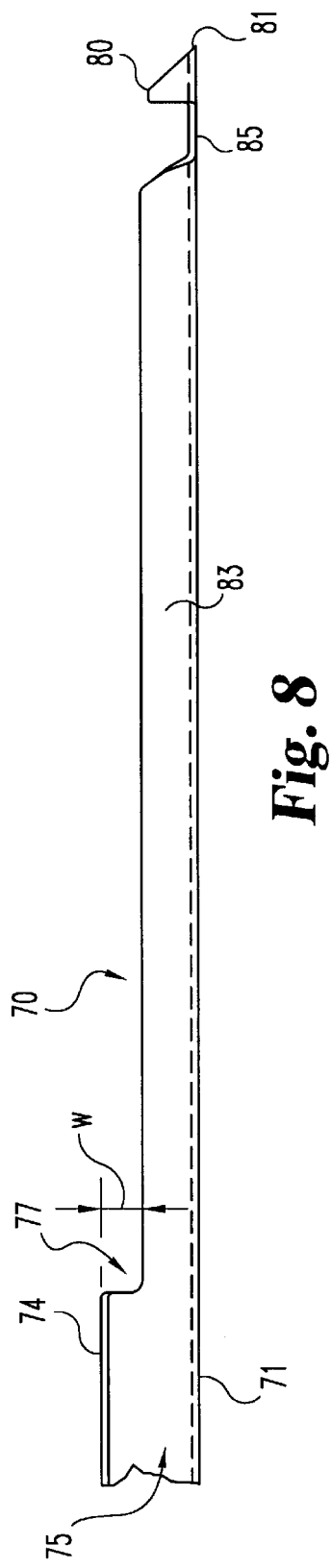
Fig. 7
Fig. 8

US 6,416,484 B1

BIOPSY EXTRACTOR

FIELD OF THE INVENTION

The invention relates generally to medical devices and more specifically to biopsy and tissue sampling and harvesting devices and methods.

BACKGROUND OF THE INVENTION

It is often desirable to remove tissue from an animal for pathological evaluation, transplantation or scientific study. For example, bone marrow is sampled to verify a diagnosis, assess the extent of disease, and evaluate the damage caused by certain cancer treatments such as high dose radiation therapy and chemotherapy. Bone marrow is also harvested for transplantation in the treatment of certain hematologic diseases and cancers related to bone marrow function. The biopsy needle is still required and is inserted into the bone marrow core tissue.

Unfortunately, extracting a core of bone marrow has always been very painful for the patient or donor. Using prior art devices and methods, the biopsy needle must be aggressively twisted, rotated and oscillated to separate the core sample from the surrounding bone marrow tissue. This is aggravated by the relatively low success rate in obtaining a satisfactory sample from a single insertion into the bone. Further, it can be difficult to retain the sample during removal of the biopsy needle from the tissue which leads to repetition of the painful procedure. The aggressive movement of the needle and the design of prior art devices often destroys the architecture of the core, which can lead to difficulties in diagnosis and the need to make additional insertions into the patient. This is further a problem because the pain associated with the procedure can be a deterrent to potential bone marrow donors who must endure repeated marrow extractions to harvest a sufficient amount of bone marrow.

U.S. Pat. No. 5,333,619 to Burgio discloses a plate for use with a typical bone marrow biopsy device, which includes a biopsy needle having a distal tapered portion. The needle of such devices is tapered to reduce the diameter of the core of tissue to be severed and to trap the severed core within the lumen. The plate of Burgio is a thin curved plate which is designed to be inserted between the inner surface of the needle and the external surface of the biopsy tissue cylinder. The device is advanced within the needle until the taper of the needle forces it to put pressure on the biopsy cylinder. At this point, the entire needle assembly is rotated and rocked to loosen the tissue sample from the surrounding tissue. According to Burgio, it is critical that the plate be thin enough to fit between the needle wall and the biopsy cylinder yet retain sufficient rigidity to withstand the procedure. The entire biopsy assembly is removed to sever the sample from the surrounding tissue. The plate is then removed from the lumen of the biopsy needle to obtain the biopsy tissue.

The device of Burgio, while an improvement over prior biopsy devices, has disadvantages. The Burgio device has an opening for receiving the sample that is about one third of the overall diameter of the plate member. This results in crushing of the tissue as the plate member is forced between it and the needle. As the plate member is forced into the smaller diameter portion of the biopsy needle, the plate member is squeezed, further crushing the sample. Moreover, Burgio is similar to prior devices because it requires rotation, rocking and removal of the needle to sever the sample from the tissue. This causes pain to the patient and further crush artifact of the sample. Secondly, the needle is removed before the tissue sample is verified. If the sample is not adequate, the biopsy needle must be reinserted at a different location.

U.S. Pat. No. 4,785,826 to Ward also discloses an inner member for insertion into the biopsy needle after tissue has been pulled into the lumen. The inner member has one or more flexible segments which bend or deflect upon reaching a shoulder or area of reduced diameter at the distal end of the cannula to capture the tissue sample. The disadvantage of this device is that the entire instrument must be removed to retrieve the tissue sample; thus, requiring the entire procedure to be repeated if a second sample is required. In addition, care must be taken not to permanently bend the flexible members during the process. Doing so will not allow the inner member to return to its original shape which would make expulsion of the sample difficult.

A need has remained for devices that can reliably sever a bone marrow sample from surrounding tissue and trap the sample without crush artifact. There is also a need for devices that minimize trauma to surrounding tissue and reduce pain and discomfort for patients.

SUMMARY OF THE INVENTION

The present invention provides devices, assemblies and methods for extraction of tissue from animals. This invention is particularly useful in the removal of bone marrow.

In accordance with one aspect of the invention, a bone marrow biopsy assembly is provided for extracting bone marrow tissue samples. The assembly includes an outer cannula or biopsy needle having a tapered distal end and an extractor including an inner cannula sized for slidable insertion into the proximal end of the outer cannula. The extractor includes a cannula and a distal working end. The distal working end has a diameter larger than the diameter of the tapered portion of the biopsy needle lumen. The working end includes a body portion adjacent the cannula and a cutting head having a cutting tip. A hinge is engaged between the body portion and the cutting tip. The hinge allows the cutting head to bend when pushed into the tapered distal end of the outer cannula allowing the cutting tip to sever the tissue sample.

In use, the extractor is inserted into the outer cannula until the cutting head contacts the tapered end of the outer cannula. Pressure is applied to the extractor causing the cutting head to bend allowing the cutting tip to sever the tissue sample. The bending of the cutting also secures the sample in the inner cannula. The outer cannula can be left in place until a good sample is verified. Subsequent extractions can be performed by adjusting the biopsy needle and inserting another extractor if additional samples are necessary.

One object of the present invention is to provide improved devices and assemblies for extracting tissue samples. A further object is to provide a device that allows the procedures of sampling and harvesting tissue to be repeated if necessary without having to make another hole in the bone cortex. These and other objects, advantages, and benefits are accomplished according to the devices, assemblies and methods of the present invention.

DESCRIPTION OF THE FIGURES

FIG. 7 is a top elevation view of the extractor.

FIG. 8 is a front view of the extractor of FIG. 7.

DESCRIPTION OF THE PREFERRED EMBODIMENTS

Figure 1:
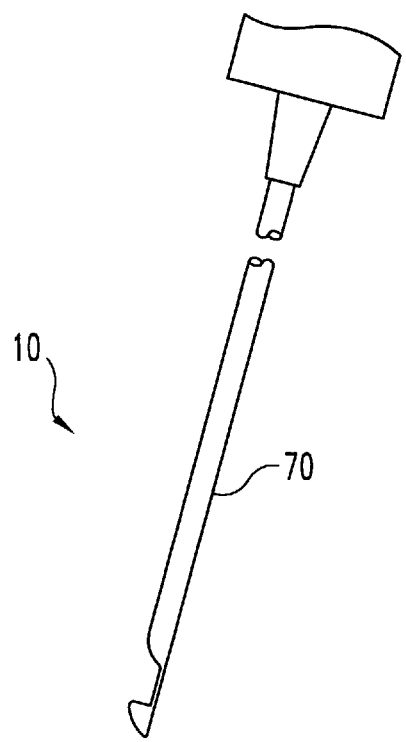
FIG. 1 is a perspective view of the biopsy assembly and the extractor according to a preferred embodiment of the invention.
Figure 1:
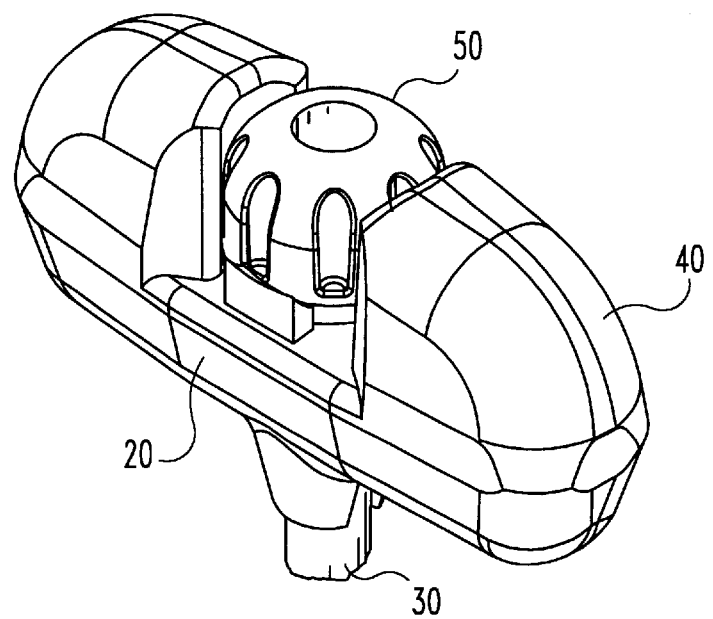

For the purposes of promoting an understanding of the principles of the invention, reference will now be made to the embodiments illustrated in the drawings and specific language will be used to describe the same. it will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides biopsy extractors, biopsy assemblies and methods of use of the extractors and assemblies. The present invention makes bone marrow biopsies easier, safer and more efficient with less pain and discomfort to the patient. Use of the present invention also results in better biopsy samples in which the architecture of the sampled tissue is preserved without crush artifact thus making more accurate diagnosis possible.

Figure 3:
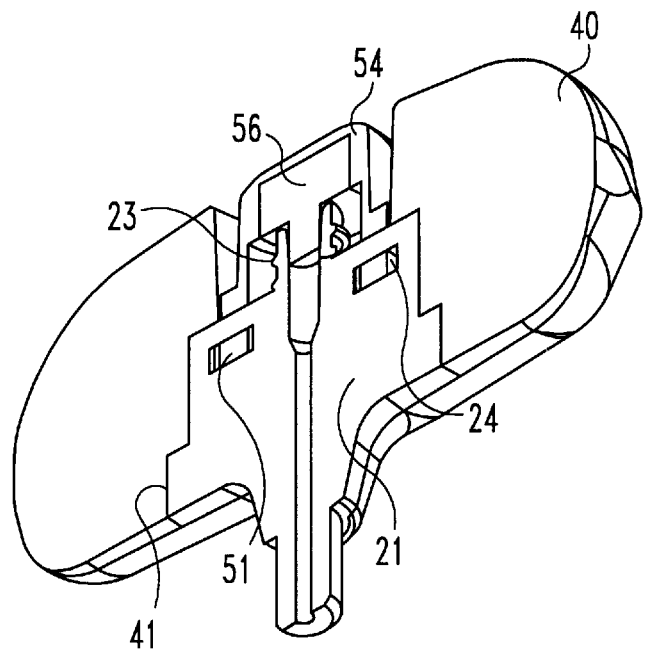
FIG. 3 is a perspective view of the handle detail showing the insertion point of a biopsy needle.
Figure 4:
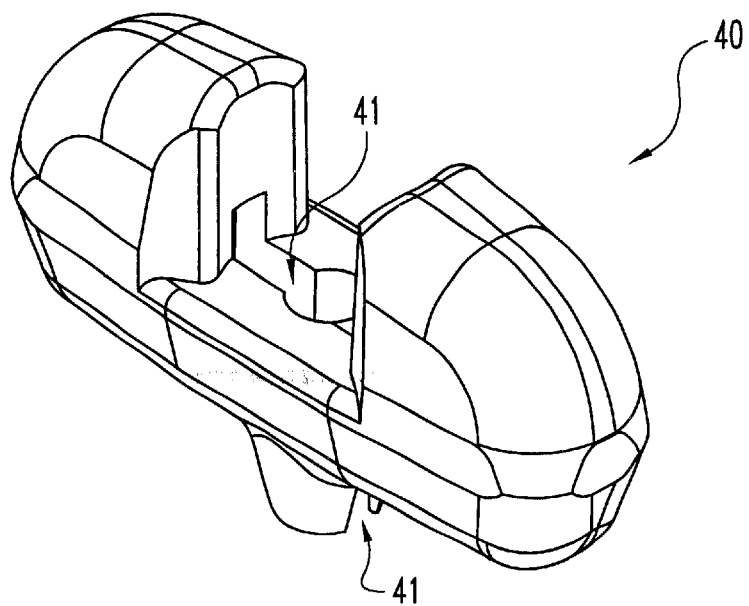
FIG. 4 is a perspective view of the outer portion of the handle assembly.

An assembly 10 according to one embodiment of the invention is shown in FIG. 1. The assembly 10 includes an introducer 20, a handle 40, a stylet 50 and an extractor 70. As shown more clearly in FIG. 2, the introducer 20 includes an engagement member 21 for engaging the biopsy needle 30 to a handle 40. Engagement member 21 defines a passageway 25 in communication with the lumen 35 of the biopsy needle 30. Preferably, the engagement member will snap fit into the handle. As shown in FIGS. 3 and 4, handle 40 defines a slot 41 for receiving the engagement member 21. In this embodiment, the handle 40 is disengageable from the biopsy needle 30 so that the handle can be reused while the biopsy needle is disposable or can be autoclavable. This makes the invention less costly because it is not necessary to dispose of or autoclave the handle after each use. It also broadens the options for forming handle 40 in ergonomic shapes and for using materials that will withstand the pressure during insertion of the biopsy needle into bone.

Figure 5:
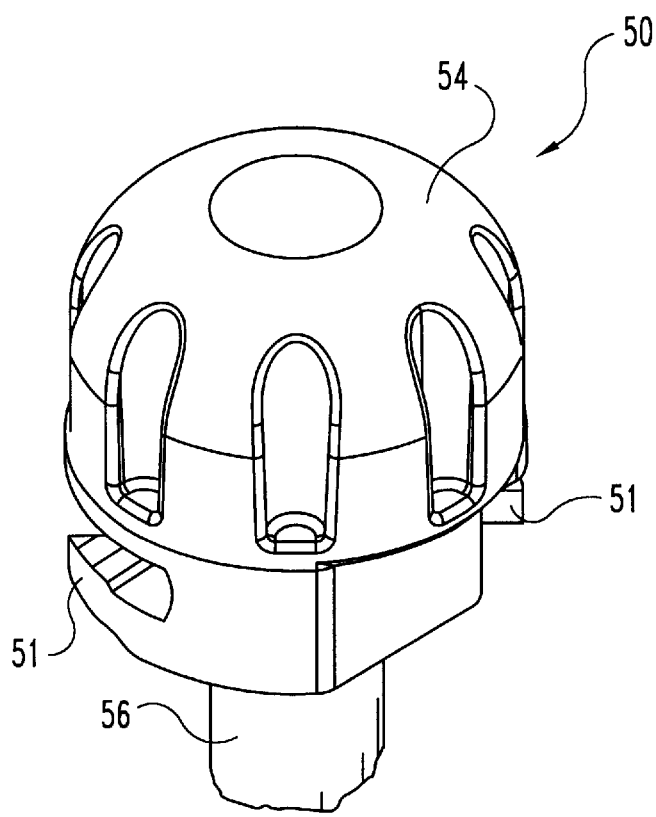
FIG. 5 is a perspective view of the upper end of the stylet

The engagement member 21 includes engaging means for engaging a stylet 50 and a syringe (not shown). In the embodiment shown in FIGS. 2 and 5, the engaging means includes threads 23 on a post 22 for engaging threads inside on a Luer lock syringe. The engaging means of this embodiment also includes grooves 24 defined in the engagement member 21 for receiving engaging arms 51 extending from the cap member 54 of the stylet 50. The shaft 56 of the stylet 50 is positionable through the passageway 25 of the engagement member 21 and the lumen 35 of the biopsy needle 30. Preferably, stylet 50 will be provided with a sharpened tip (not shown) that extends from the end of biopsy needle to facilitate insertion through tissue and bone.

Figure 2:
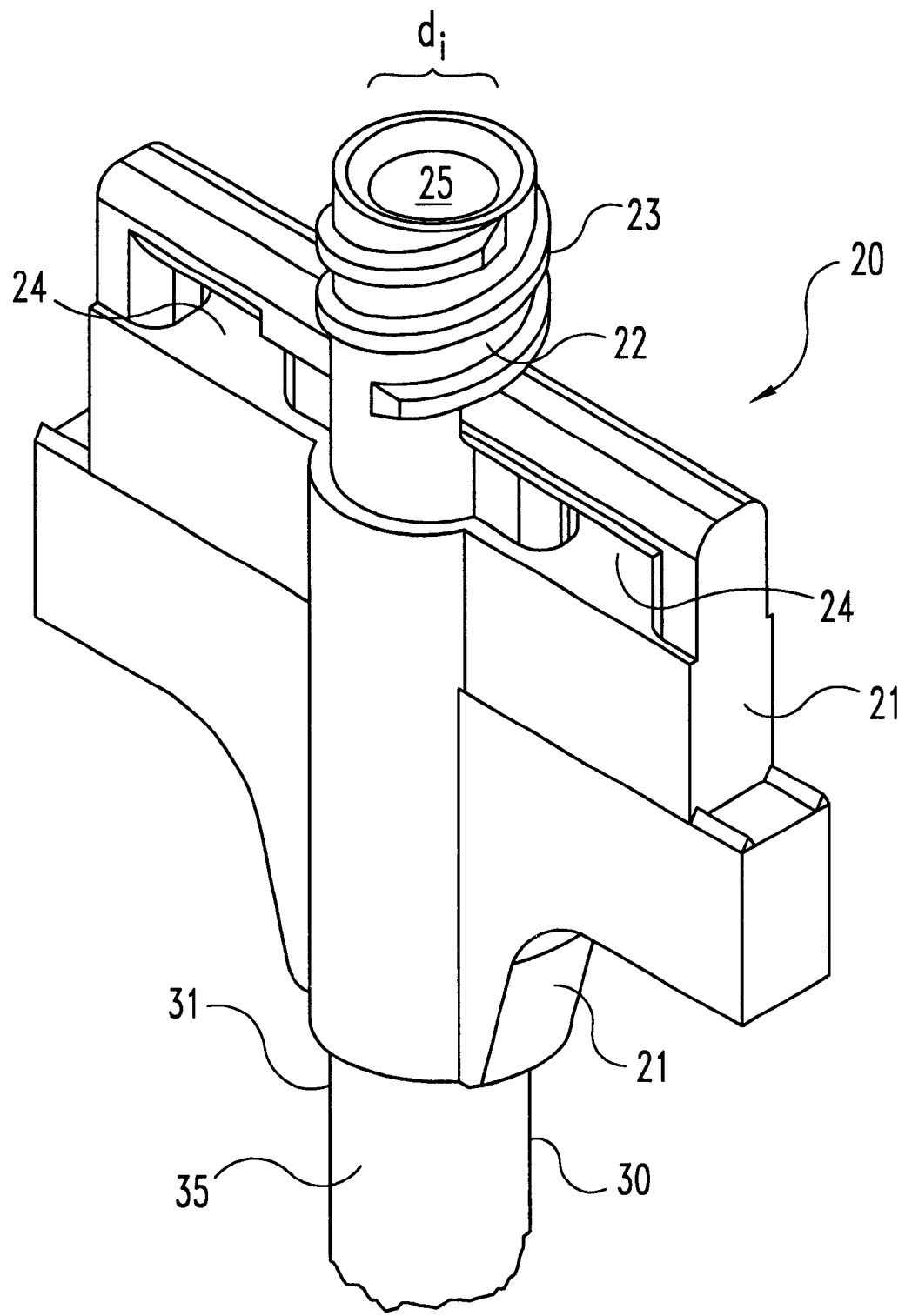
FIG. 2 is a perspective view of the introducer assembly according to the invention.
Figure 6:
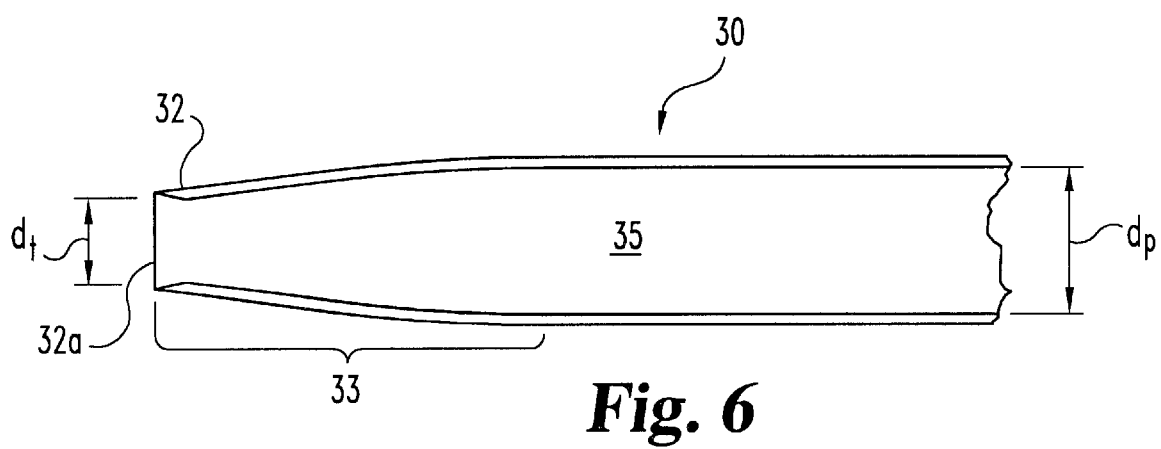
FIG. 6 is a side view of a biopsy needle.

Referring now to both FIGS. 2 and 6, biopsy needle 30 comprises a hollow, tubular outer member having a proximal end 31 and a distal end 32. Needle 30 defines a proximal opening (not shown) at the proximal end 31 and a distal opening 32a at the distal end 32. Needle 30 further defines a lumen 35 axially extending from the proximal end 31 to the distal end 32 and which communicates with the proximal and distal openings. Lumen 35 tapers near the distal end 32 to form a tapered portion 33 that has a diameter $d_t$ that is smaller than the diameter $d_p$ of the more proximal portion of the lumen 35. In prior devices, the purpose of the tapered portion 33 was to trap biopsy material and facilitate severing the sample from its attachment site within the tissue. This was not effective however, and the use of such devices typically required multiple stabs to achieve sufficient tissue for pathology, which caused increased trauma to the tissue and pain for the patient. This is aggravated further during tissue harvesting for transplantation because a larger quantity of tissue is required.

Assembly 10 further includes a biopsy extractor 70 as shown in FIGS. 7 and 8. Extractor 70 includes an elongated cannula 71 that is slidable within the lumen 35 of the biopsy needle 30. Cannula 71 has a cannular wall 74 that defines a passageway 75, which extends axially between a proximal end 72 and a distal end 73. Extractor 70 further includes a distal working end 76, which has a deformable portion and a diameter $d_e$ that is larger than the smaller diameter $d_t$ of the lumen (FIG. 6). Working end 76 includes a cutting head 80 that includes a cutting tip 81. Working end 76 preferably defines an open channel 77 in communication with passageway 75. Channel 77 and cannular wall 74 form a bed 78 for a tissue sample.

Figure 9:
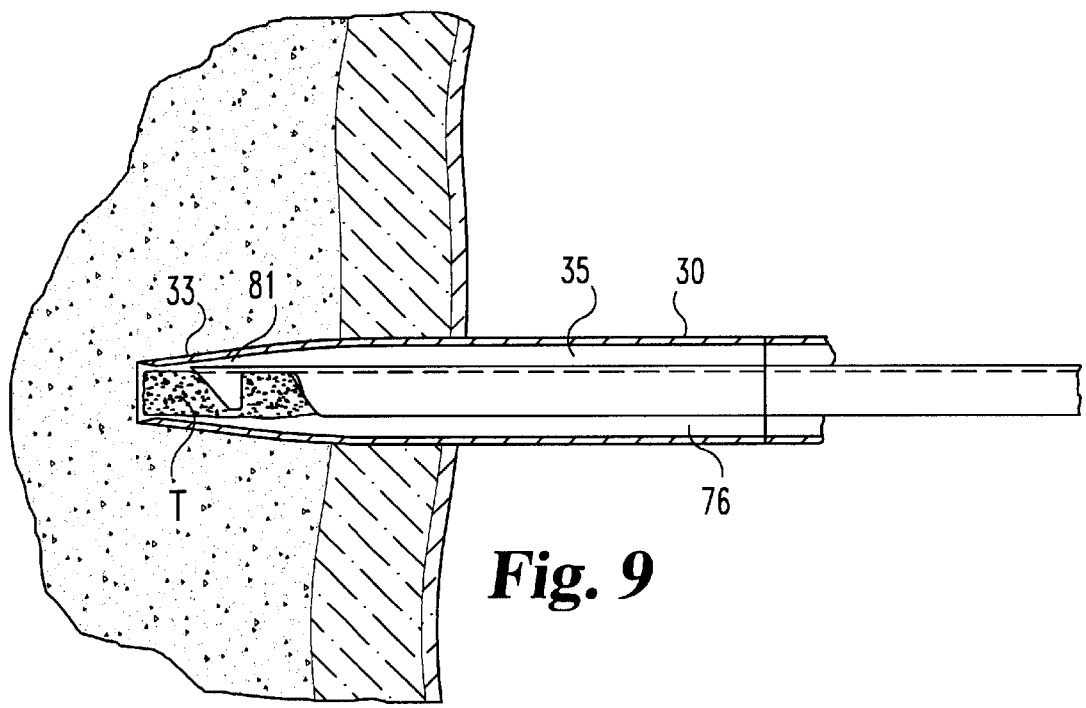
FIG. 9 shows the insertion of the working end of the extractor between the wall of a biopsy needle and the tissue sample.

The working end 76 is configured to be inserted between the wall of the biopsy needle 30 and a core of tissue T within the lumen 35 as shown in FIG. 9. The present invention provides features for reducing or eliminating crush artifact. One way to decrease damage to the tissue core T is to adjust the size of the working end 76 that is forced underneath the core. Referring again to FIGS. 7 and 8, preferably, channel 77 has a width w that is more than one third of the diameter $d_e$ of the working end 76. Most preferably, width w is about one half of diameter $d_e$. Increasing width w decreases damage to the core T as the working end 76 is pushed between the core T and the needle 30. Due to the deformable portion of the extractor of this invention, the device does not clamp down and around the sample as in the prior art.

Figure 10:
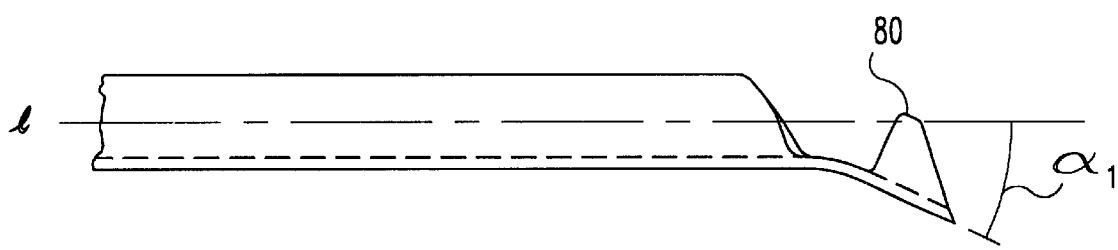
FIG. 10 is a side view of the working end of the extractor showing the bend angle of the cutting head.

Another feature of this invention that reduces crush artifact is that in some embodiments, the cutting head 80 is bent away from the longitudinal axis ι of the channel 77 as shown most clearly in FIG. 10. Preferably, cutting head 80 is bent away at an angle $\alpha_1$ of about 0° to about 45°, with a most preferred angle $\alpha_1$ of about 0°. Bending the cutting head away from or having the cutting head parallel with axis $\alpha_1$ further reduces damage to the core T as the cutting head 80 is positioned between the core T and the biopsy needle 30.

Figure 11:
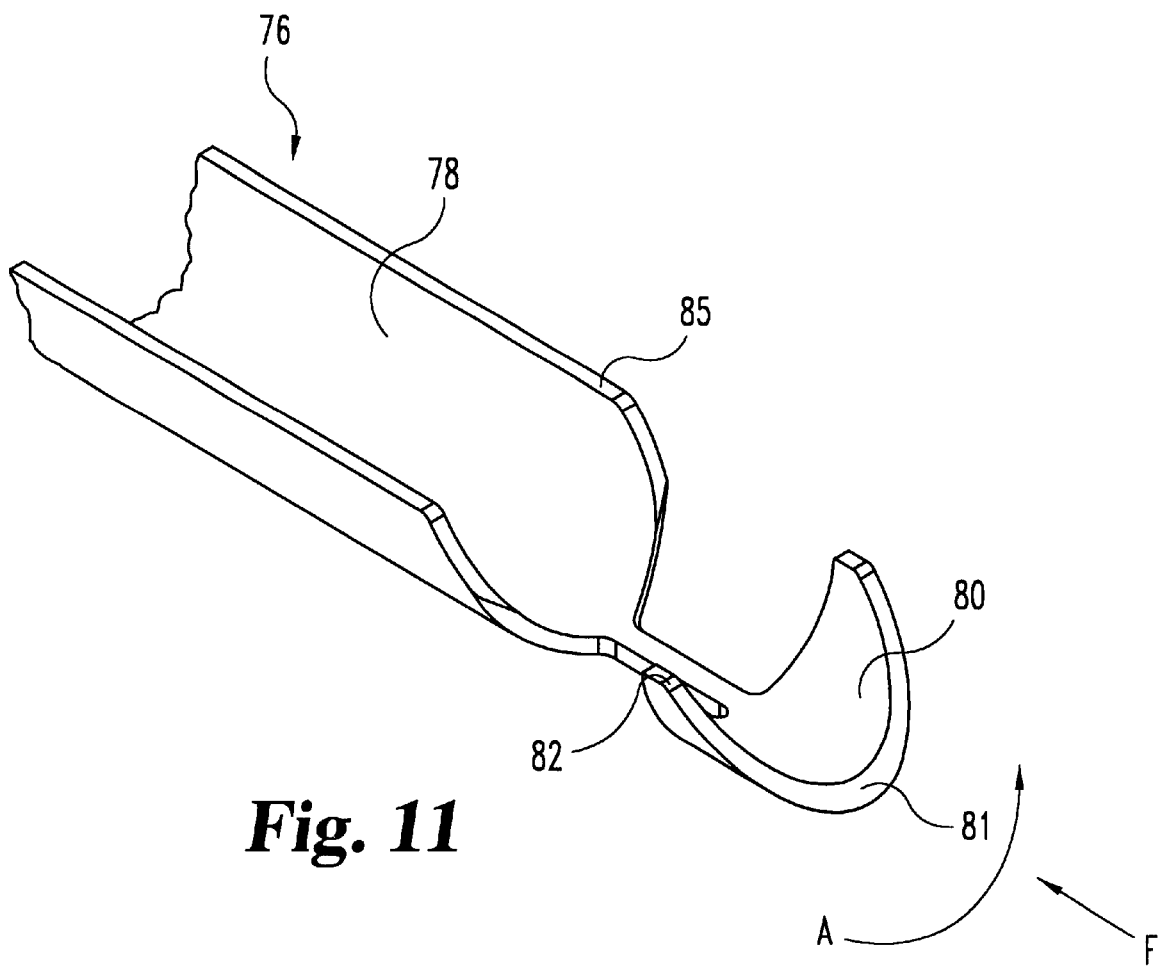
FIG. 11 is a perspective view of the working end of the extractor showing the wings on the cutting head.
Figure 12:
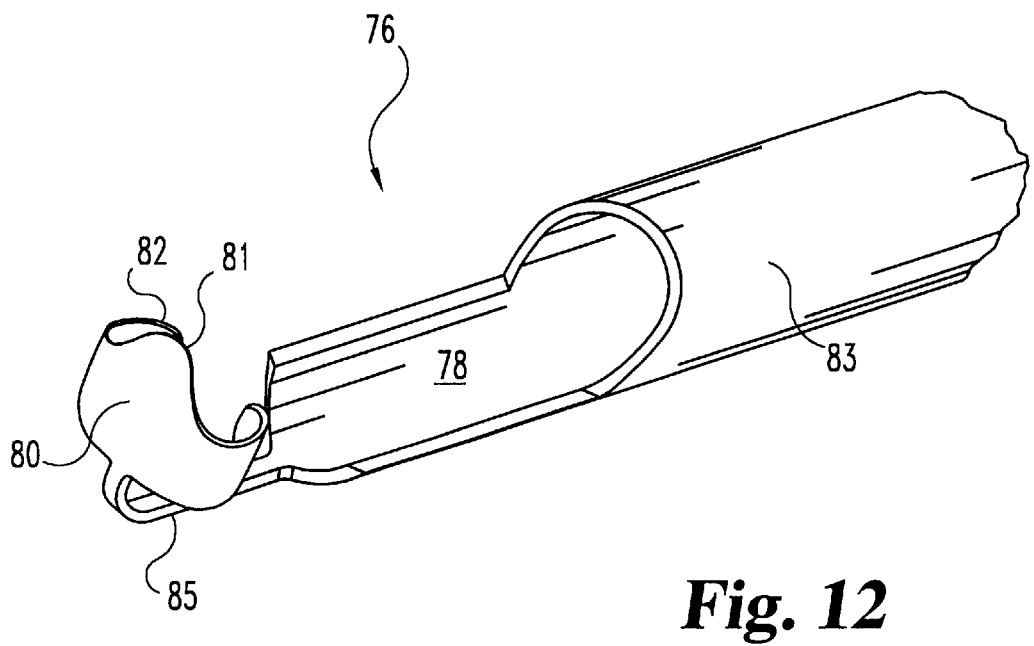
FIG. 12 is a perspective view of the working end of the extractor showing the cutting head bent to retain the tissue sample.
Figure 13:
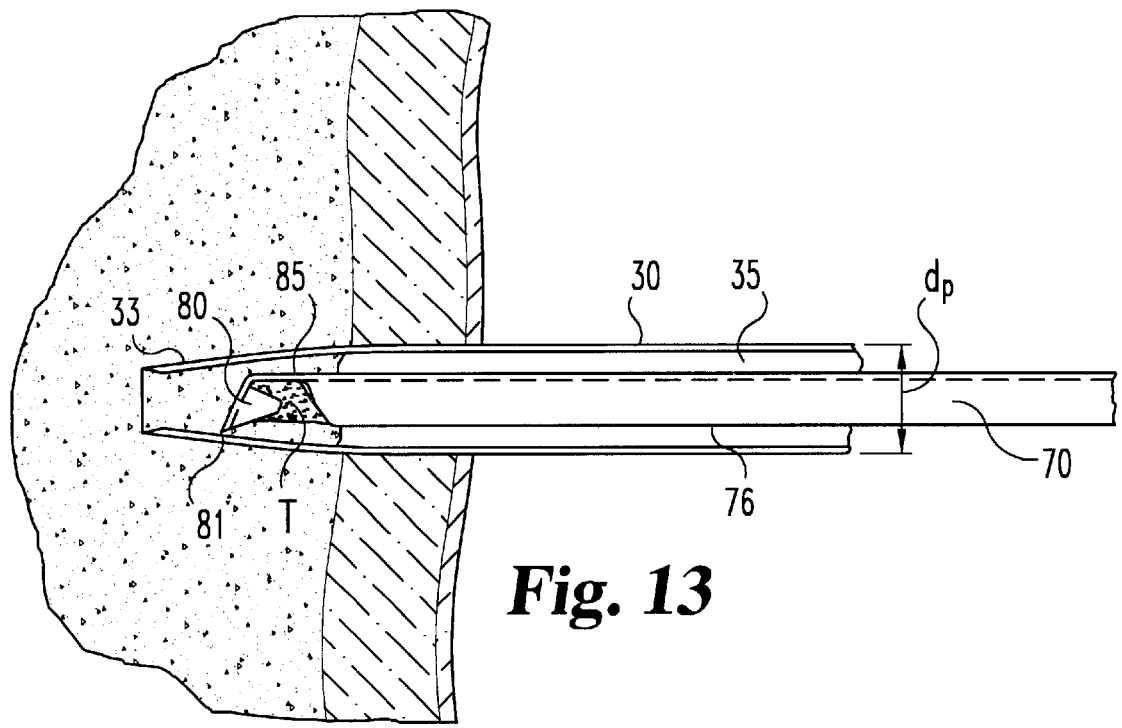
FIG. 13 shows the working end of the extractor with the cutting head bent severing and retaining the tissue sample.
Figure 14:
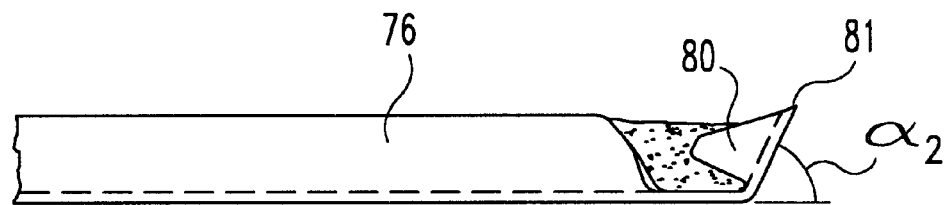
FIG. 14 is a side view of the extractor working end showing the bend angle of the cutting head after deformation to sever and retain the sample.

The extractors of this invention also preferably provide deforming means for inelastically deforming the distal working end 76 to trap a biopsy sample within the bed 78. In preferred embodiments, the deforming means is a hinge engaged between the cannula and the cutting tip. In the embodiment shown in FIGS. 7 and 8, the hinge 85 is a neck portion, or narrowed area, disposed between the body portion 83 of the distal working end 76 and the cutting head 80. Hinge 85 allows working end 76 to be deformed with cutting head 80 moving in the direction of arrow A upon receiving a force F as shown in FIGS. 11 and 12. Referring now to FIG. 13, as cutting head 80 is advanced through the lumen 35 of the biopsy needle 30 and contacts the tapered portion 33, the neck portion 85 begins to bend and the cutting head 80 is deflected. As the cutting head 80 is deflected, the cutting tip 81 will sever the core T within the bed 78 from the remaining tissue. Preferably, the cutting head 80 will be deflected at an angle $\alpha_2$ of no more than about 90° (FIG. 14). During the deformation of the cutting head, the material of the hinge 85 will exceed its elastic limit. The hinge 85 will hold its deflected position as shown in FIG. 13 as the extractor 70 is backed out of the lumen 35 and thus will keep the core T trapped within the bed 78 until it is removed by the physician.

Referring again to FIGS. 11 and 12, in preferred embodiments, the extractor 70 includes one or more wings 82 on the cutting head 80 adjacent the cutting tip 81. Wings 82 provide a ramp that guides the core out of the bed when the extractor has been removed and an obturator is inserted into the passageway to eject the core.

Figure 15:
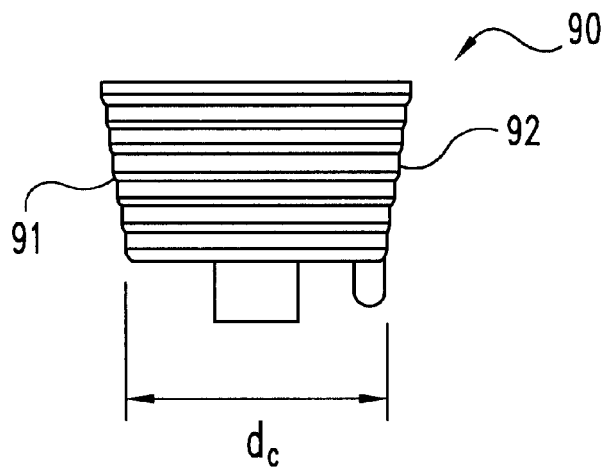
FIG. 15 is a view of the proximal end of the extractor showing one embodiment of the grasping element.

The proximal end 72 of the extractor 70 may be provided with a suitable grasping element. In a preferred embodiment shown in FIGS. 7 and 15, the grasping element is a cap 90 disposed over the proximal end 72. The outer surface 91 of the cap member 90 defines ridges 92 to facilitate manipulating the extractor 70 within the lumen 35. The cap 90 also, in this embodiment, has a diameter $d_c$ that is larger than the diameter $d_i$ of the passageway 25 of the introducer 20 so that the cap 90 is a stop member to prevent over-insertion of the extractor 70 into the lumen 35 of the biopsy needle 30.

Figure 16:
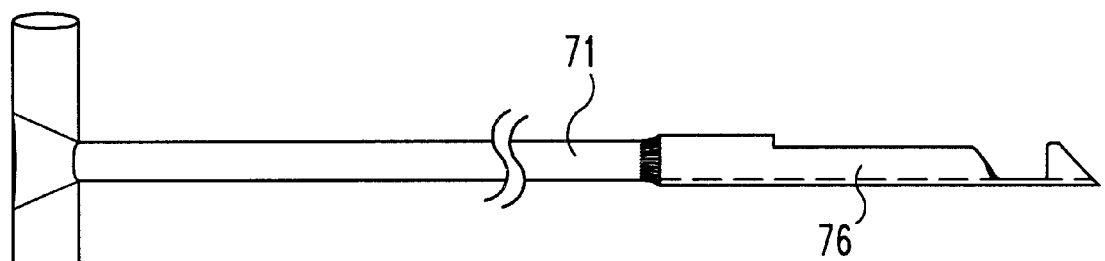
FIG. 16 is a side view showing the working end of the extractor attached to a handle.

The present invention can be constructed of any suitable material in any suitable size. For example, the cannula 71 of the extractor can be composed of a material such as plastic while the working end 76 is formed of metal with the cannula attached to the working end 76 as shown in FIG. 16. In preferred embodiments, the cannula 71 and the working end 76 are integral and are composed of a surgical grade stainless steel.

Figure 17:
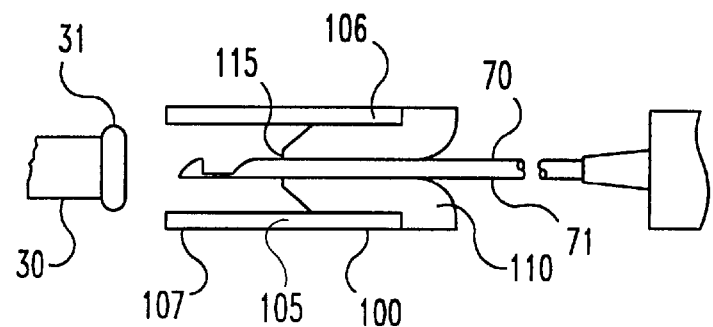
FIG. 17 shows the guide member assembly for transporting the extractor and inserting it into the lumen of a biopsy needle.

The present invention also provides a guide member 100 for transporting the extractor 70 and inserting it into the lumen of the biopsy needle 30 as shown in FIG. 17. The guide member 100 includes a sleeve 105 having a first end 106 and an opposite second end 107, which is engageable to the proximal end 31 of the biopsy needle 30. A friction collar 110 is disposed at the first end 106. The friction collar 110 defines a passageway 115 having a diameter sufficient to receive and releasably hold the cannula 71 of the extractor 70 with the distal working end 76 adjacent the second end 107 of the sleeve 105. The extractor 70 can then be disengaged from or pushed through the friction collar 110 to insert the working end 76 into the lumen 35 of the biopsy needle 30. The guide member allows the extractors of this invention to be transported and then inserted into the biopsy needle safely without risk of damage to the working end.

Figure 18:
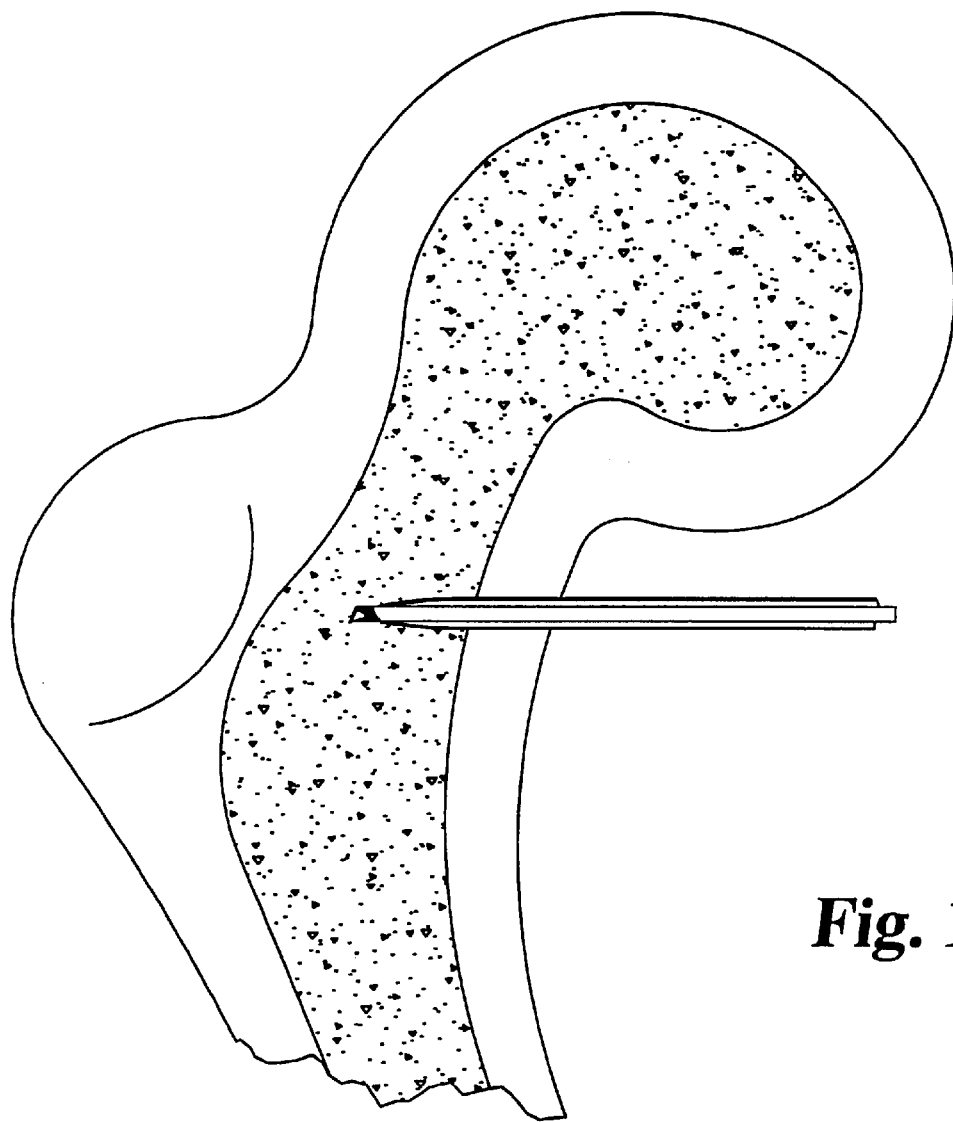
FIG. 18 depicts a method of using the invention by first inserting a biopsy needle into the tissue to be sampled.

The present invention also provides methods for obtaining a bone marrow biopsy from a patient. The methods include inserting the distal end 32 of the outer member or biopsy needle 30 into tissue to collect a sample within the lumen 35 of the outer member 30 as shown in FIG. 18. The next step of the methods includes advancing the working end 76 of the extractor 70 through the lumen 35 of the outer member 30 between the sample T and the outer member 30 until the tip 81 reaches the tapered portion 33 as shown in FIG. 9. Referring again to FIG. 13, the working end 76 is then further advanced against the tapered portion 33 until the working end 76 deforms so that the cutting tip 80 severs the sample core T from the tissue and the working end 76 traps the core T. It is not necessary to rotate the extractor as in prior devices to trap the core within the bed. The methods also include removing the extractor from the lumen with the severed sample trapped within the extractor. After the extractor is removed, the sample can be examined. If it is not deemed to be sufficient, a second extractor can be used to obtain a second sample. The distal end of the outer member can be moved to a new location within the tissue before obtaining the second sample without the need for a second insertion of the biopsy needle.

EXAMPLE

The present invention shall be more concretely explained with the following example, which is to be considered merely representative of the present invention and thus should not be considered as limiting.

Procedures

A is prepared for a bone marrow biopsy procedure. Lidocaine, is injected close to the bone. The physician grasps the handle of the biopsy device, with the stylet within the lumen of the outer member and punches the device through the skin and tissue and into the iliac crest. The stylet is then removed and the biopsy needle is pushed further into the bone to force tissue into the lumen. An obturator is inserted into the lumen to roughly measure the height of the tissue core in the lumen.

After the obturator is removed, the distal end of the extractor is placed into the lumen and pushed forward between the core and the internal surface of the outer member until the distal end reaches the tapered portion of the outer member. As the distal end is forced against the smaller diameter of the tapered portion, the distal end bends at the hinge portion and the cutting tip severs the core from the tissue. Pushing the distal end against the tapered portion also deforms the wings to trap the severed core within the bed. The extractor is then withdrawn from the outer member. The tissue core is removed by inserting the obturator through the proximal opening of the extractor and ejecting the core. The ramp formed by the wings facilitates removal of the core.

If it is determined that additional sampling is required, the outer member is repositioned within the bone without need to remove the outer member from the patient and then reinsert it at a new location. A second extractor is then used to trap and remove a second core. Once the physician is satisfied that an adequate sample has been obtained, the outer member is removed from the patient.

Results

The present invention results in less crush artifact because it is unnecessary to rotate the extractor within the outer member. Further, in preferred embodiments wherein the channel defined in the extractor has a width of about one half of the diameter of the distal end of the extractor, driving the extractor between the core and the lumen wall causes less damage to the core than prior devices that have a channel width of only about one third of the distal end diameter.

The present invention also causes less tissue trauma and pain to the patient because the physician can determine whether the biopsy sample is adequate while leaving the biopsy needle in place. If additional samples are required, the biopsy needle can be repositioned and a second extractor can be used to obtain a second sample. There is no need for more than one insertion of the biopsy needle.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A bone marrow biopsy assembly, comprising:
    a hollow, tubular outer member having a proximal end and a distal end and defining a lumen axially extending therethrough, said lumen tapering to a smaller diameter at said distal end to form a tapered portion, said outer member defining a proximal opening at said proximal end and a distal opening at said distal end; and
    a biopsy extractor having
        an elongated cannula slidably disposed within said lumen,
        an inelastically deformable distal working end having a cutting tip and a diameter larger than said smaller diameter of said lumen, and
        a hinge engaged between said cannula and said cutting tip.

2. The assembly of claim 1, further comprising a wing disposed on said distal working end adjacent said cutting tip.

3. The assembly of claim 1, further comprising an open channel defined in said working end adjacent said hinge.

4. The assembly of claim 1, further comprising a guide member, the guide member including:
    a sleeve having a first end and an opposite second end engageable to said proximal end of said outer member; and
    a friction collar disposed at said first end, said friction collar defining a passageway having a diameter sufficient to receive and releasably hold said elongated cannula with said distal working end adjacent said first end of said sleeve.

5. The assembly of claim 1, further comprising a stylet slidable within said lumen.

6. The assembly of claim 5 where in said stylet has a tissue piercing tip.

7. A method for obtaining a bone marrow biopsy sample, comprising: providing an assembly of claim 1;
    inserting the distal end of the outer member into tissue to collect a sample within the lumen of the outer member;
    advancing the working end of the extractor through the lumen of the outer member between the sample and the outer member until the tip reaches the tapered portion;
    further advancing the working end against the tapered portion until the working end inelastically deforms so that the cutting tip severs the sample from the tissue and the working end traps the sample.

8. The method of claim 7 further comprising:
    removing the extractor from the lumen with the severed sample trapped within the extractor.

9. The method of claim 8 further comprising:
    after removing the extractor from the lumen, inserting the distal working end of a second extractor into the lumen to obtain a second sample.

10. The method of claim 9 further comprising moving the distal end of the outer member to a new location within the tissue before obtaining the second sample.

11. A bone marrow biopsy extractor for use with a biopsy needle defining a lumen tapering to a smaller diameter at a distal end, the extractor comprising:
    an elongated cannula defining a passageway axially extending therethrough, said cannula slidable within the lumen; and
    an inelastically deformable distal working end having a diameter larger than the smaller diameter of the lumen and defining a channel in communication with said passageway, said working end including a body portion adjacent said cannula and a cutting head having a cutting tip, said distal working end further having a hinge engaged between said body portion and said cutting tip.

12. The extractor of claim 11 wherein said cannula is formed of a plastic composition and said working end is formed of metal.

13. The extractor of claim 11 wherein said extractor is stainless steel.

14. The extractor of claim 11 wherein said cutting head is bent away from an axis defined by said channel of said working end.

15. The extractor of claim 14 wherein said cutting head is bent away at an angle of about 5° to about 45°.

16. The extractor of claim 15 wherein said cutting head is bent away at an angle of about 45°.

17. A bone marrow biopsy extractor for use with a biopsy needle defining a lumen tapering to a smaller diameter at a distal end to form a reduced portion, the extractor comprising:
    an elongated cannula slidable within the lumen, said cannula having a cannular wall defining a passageway axially extending therethrough; and
    a distal working end having a diameter larger than said smaller diameter of the lumen, said working end defining
        a body portion connected to said cannula, said body portion defining a channel in communication with said passageway and forming a bed for a tissue sample,
        a cutting head including a tissue cutting tip integral with at least one wing, and
        a neck portion connecting said body portion with said cutting head, said neck portion bendable when said cutting head is advanced against the reduced portion.

18. The extractor of claim 17 wherein said channel has a width about one half of said diameter of said distal working end.

19. The extractor of claim 17 wherein said cutting head is bent away from an axis defined by said channel of said working end.

20. The extractor of claim 19 wherein said cutting head is bent away at an angle of about 5° to about 45°.

21. The extractor of claim 20 wherein said cutting head is bent away at an angle of about 45°.

22. A bone marrow biopsy extractor for use with a biopsy needle defining a lumen tapering to a smaller diameter at a distal end, the extractor comprising:

an elongated cannula defining a passageway axially extending therethrough, said cannula having a cannular wall defining a passageway axially extending therethrough, said cannula slidable within the lumen;

a deformable distal working end defining a channel in communication with said passageway, said channel and said cannular wall forming a bed for a tissue sample, said working end having a diameter larger than the smaller diameter of said lumen; and deforming means for inelastically deforming said distal working end to trap a biopsy sample within said bed.

23. A bone marrow biopsy assembly, comprising:

a hollow, tubular outer member having a proximal end and a distal end and defining a lumen axially extending therethrough, said lumen tapering to a smaller diameter at said distal end to form a tapered portion, said outer member defining a proximal opening at said proximal end and a distal opening at said distal end; and a biopsy extractor having an elongated cannula slidably disposed within said lumen, said cannula defining a passageway extending axially therethrough, a deformable distal working end having a cutting tip and a diameter larger than said smaller diameter of said lumen, said distal working end defining a channel in communication with said passageway, a hinge engaged between said cannula and said cutting tip, and a wing disposed on said distal working end adjacent said cutting tip.

24. The bone marrow biopsy assembly of claim 23 wherein said cutting head is bent away from an axis defined by said channel of said working end.

25. The bone marrow biopsy assembly of claim 24 wherein said cutting head is bent away at an angle of about 5° to about 45°.

26. The bone marrow biopsy assembly of claim 25 wherein said cutting head is bent away at an angle of about 45°.

27. The bone marrow biopsy assembly of claim 23 wherein said channel has a width about one half of said diameter of said distal end.

* * * * *